United States Patent [19]

Heywang-Koebrunner

[11] Patent Number: 5,702,405
[45] Date of Patent: Dec. 30, 1997

[54] STEREOTACTIC AUXILIARY ATTACHMENT FOR A TOMOGRAPHY APPARATUS FOR TOMOGRAM GUIDED IMPLEMENTATION OF A BIOPSY

[75] Inventor: Sylvia Heywang-Koebrunner, Engelsdorf, Germany

[73] Assignee: Siemens Aktiengesellschaft, Munich, Germany

[21] Appl. No.: 564,645

[22] Filed: Nov. 29, 1995

[30] Foreign Application Priority Data

Nov. 30, 1994 [DE] Germany .................... 44 42 609.7

[51] Int. Cl.$^6$ .................................................. A61B 19/00
[52] U.S. Cl. ..................... 606/130; 604/116; 128/653.1
[58] Field of Search .......................... 606/130, 129, 606/71, 96; 128/653.1, 898; 604/116

[56] References Cited

U.S. PATENT DOCUMENTS

| | | | |
|---|---|---|---|
| 4,557,272 | 12/1985 | Carr . | |
| 4,580,561 | 4/1986 | Williamson | 606/130 |
| 5,242,455 | 9/1993 | Skeens et al. | 606/130 |
| 5,308,352 | 5/1994 | Koutrouvelis . | |
| 5,311,131 | 5/1994 | Smith . | |
| 5,353,804 | 10/1994 | Kornberg et al. | 128/754 |
| 5,435,312 | 7/1995 | Spivey et al. | 128/661.02 |

FOREIGN PATENT DOCUMENTS 43 25 206  2/1994  Germany .................... 606/130

*Primary Examiner*—Robert A. Hafer
*Assistant Examiner*—Justine R. Yu
*Attorney, Agent, or Firm*—Hill, Steadman & Simpson

[57] ABSTRACT

A stereotactic auxiliary attachment for a tomography apparatus for conducting a tomogram-guided biopsy of a female breast has two compression plates arranged to be movable toward one another for fixing the breast therebetween, with through-holes arranged in the compression plates enabling a guided access of a biopsy needle to the breast through the compression plates. The through-holes in at least one of the compression plates are arranged obliquely relative to a surface normal of a compressing surface of that compression plate thereby permitting access to all regions of the breast tissue.

5 Claims, 1 Drawing Sheet

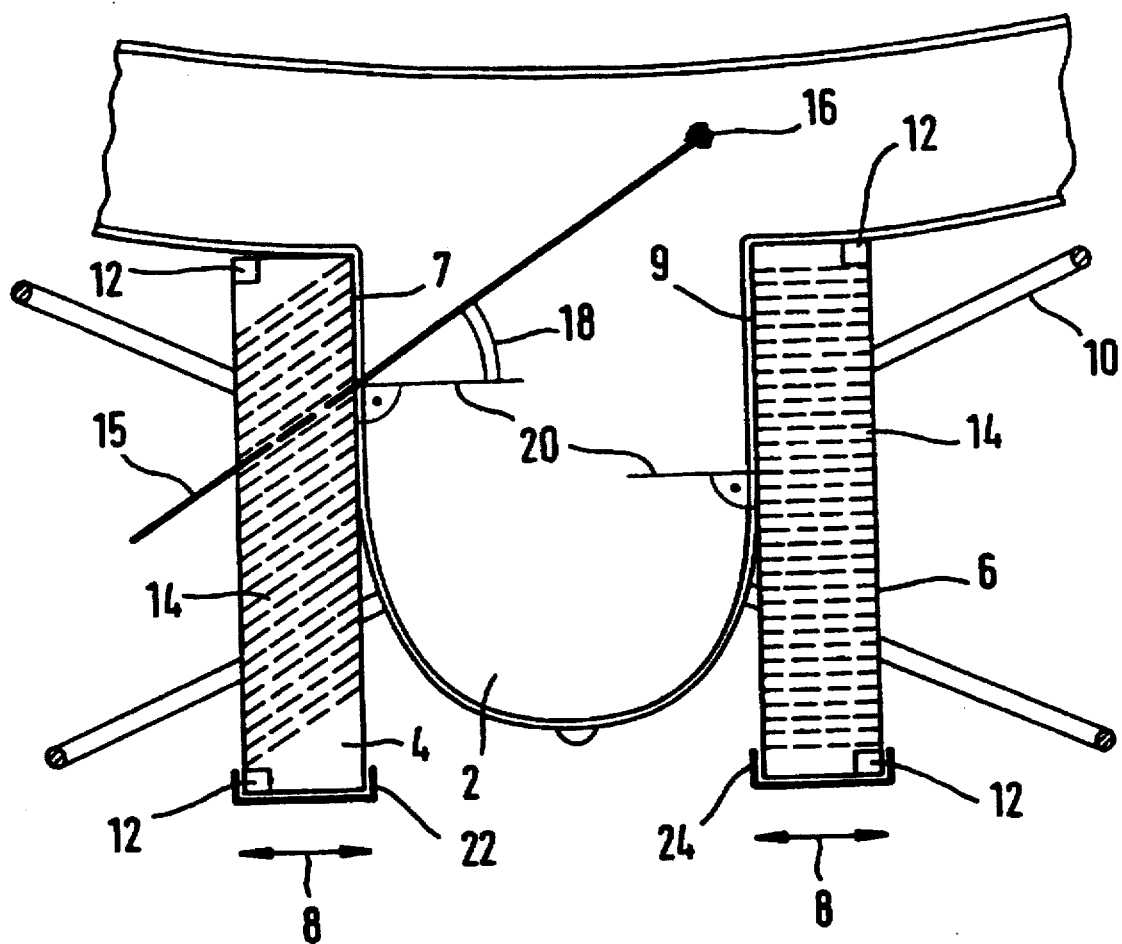

STEREOTACTIC AUXILIARY ATTACHMENT FOR A TOMOGRAPHY APPARATUS FOR TOMOGRAM GUIDED IMPLEMENTATION OF A BIOPSY

BACKGROUND OF THE INVENTION

1. Field of the Invention

The invention is directed to a stereotactic auxiliary attachment for a tomography apparatus for conducting a tomogram-guided biopsy, and in particular to such an attachment for conducting a tomogram-guided biopsy of a female breast. This known attachment has two compression plates arranged movable relative to one another for fixing the breast therebetween with at least one compression plate having through-holes that are arranged in a plane and identically directed through the compression plate, the through-holes enabling a guided access of a biopsy needle to the breast through the compression plates.

2. Description of the Prior Art

German OS 43 25 206 discloses a stereotactic auxiliary attachment for implementation of a biopsy of a female breast with the assistance of magnetic resonance tomograms. This known attachment has two compression plates arranged movable relative to one another for fixing the breast therebetween with at learn one compression plate having through-holes that are arranged in a plane and identically directed through the compression plate, the through-holes enabling a guided access of a biopsy needle to the breast through the compression plates. For examination, the breast is fixed between the compression plates. A marker means is connected to the compression plates. The marker means generates marks in the tomogram that allow an exact allocation of the lesion visible in the tomogram to the actual position in the stereotactic auxiliary attachment. One of the compression plates or both compression plates is/are provided with through-holes that enable a guided access of a biopsy needle to the beast. In this known attachment, the through-holes are all aligned perpendicularly relative to the surface of the compression plates used for fixing and compressing. Not all possible target regions wherein lesions can lie, however, can be reached with a needle via the through-holes. If a lesion lies within an inaccessible region, a biopsy cannot be implemented with this known stereotactic auxiliary attachment, particularly given lesions close to the chest wall.

U.S. Pat. No. 5,308,352 discloses a stereotactic auxiliary attachment having a bridge-like holder frame that is displaceably seated on a patient bed. A biopsy guide adjustable in different directions can be secured to the holder frame.

SUMMARY OF THE INVENTION

An object of the present invention is to provide a stereotactic auxiliary attachment for a tomography apparatus for conducting a tomogram-guided biopsy which permits arbitrarily located lesions, including lesions close to the chest wall, to be reached for the biopsy.

This object is achieved in a stereotactic auxiliary attachment having relatively movable compression through-holes in at least one of the compression plates arranged obliquely relative to a surface normal of a compressing surface of the compression plate. Lesions close to the chest wall are thus also accessible to a biopsy. The evaluation and measurement of the tomogram can ensue on a picture screen with the assistance of a computer in an embodiment wherein the application software makes available slanting lines that can be shifted over the picture screen.

In a further embodiment, the compression plates are removably arranged in a frame. Lesions close to the chest wall that lie both on the right as well as on the left are thus accessible for biopsy by interchanging compression plates. The use of one compression plate with obliquely aligned through-holes and one compression plate with perpendicularly aligned through-holes, in particular, enables access to the entire breast, including the regions close to the chest wall.

In another embodiment, marker means that generate visible marks in a tomogram are permanently allocated to the compression plates.

In another embodiment, an antenna arrangement for producing magnetic resonance tomograms is allocated in a suitable spatial relationship to the compression plates.

DESCRIPTION OF THE DRAWINGS

The single FIGURE shows an end view, partly in section, of a stereotactic auxiliary attachment for a tomography apparatus, constructed in accordance with the principles of the present invention.

DESCRIPTION OF THE PREFERRED EMBODIMENTS

The stereotactic auxiliary attachment shown in a sectional view is suitable for a tomogram-guided implementation of a biopsy of a female breast, whereby tomograms produced with the assistance of magnetic resonance are evaluated. The magnetic resonance examination is implemented with the patient in a prone position, with the breast 2 fixed between respective surfaces 7 and 9 of two compression plates 4 and 6, which are movable toward and away from one another in the examination space of the magnetic resonance apparatus (not shown in detail). For fixing the breast 2, the two compression plates 4 and 6 are moved toward one another by means of a manually actuated adjustment mechanism 5. Opening ensues in the opposite direction. The adjustment mechanism is symbolized by two double arrows 8.

The compression plates 4 and 6 are located within the detection region of two crossed conductor loops that form an antenna arrangement 10 for low-noise reception of magnetic resonance signals from the examination subject 2.

A tubular chamber 12 which is a part of a marker means is filled with a substance that can be detected with magnetic resonance. The chamber 12 extends along the circumference around that outside surface of each two compression plate 4 and 6 facing away from the examination subject. The substance generates marks in the tomogram in a defined position relative to the compression plates 4 and 6 that are used for localizing a finding of interest or a lesion 16.

Through-holes 14 are disposed in both compression plates 4 and 6 for the implementation of a biopsy. The through-holes 14 are arranged in a regular grid at spacings of, for example, 2.5 mm and enable a guided access of a biopsy needle 15 to the examination subject 2. Whereas the through-holes 14 in the compression plate 4 are aligned at an angle 18 of 30° (or approximately 30°) relative to a surface normal 20 of the surface 7 of the compression plate 4 that compresses the examination subject 2, the through-holes 14 of the compression plate 6 lie in the direction of the surface normal 20 of the compressing surface 9 of the compression plate 6, and thus in the horizontal direction.

The compression plates 4 and 6 are held by respective changing frames 22 and 24 that enable an interchange of the compression plates 4 and 6. The adjustment mechanism acts on the compression plates 4 or 6 via the changing frames 22 and 24.

Lesions lying at the right in the drawing such as the lesion 16 can be reached via obliquely directed through-holes 14 in the left compression plate 4, as shown in the drawing. After an interchange of the compression plates 4 and 6 in the changing frames 22 and 24, lesions lying at the left can then be reached via obliquely directed through-holes 14 of the compression plate 4, that is then arranged in the right-hand changing frame 24. The entire breast tissue, including regions close to the chest wall, is then accessible to a biopsy due to the different alignment of the through-holes 14 in the left compression plate 4 and the right compression plate 6.

Although modifications and changes may be suggested by those skilled in the art, it is the intention of the inventor to embody within the patent warranted hereon all changes and modifications as reasonably and properly come within the scope of her contribution to the art.

I claim as my invention:

1. A stereotactic auxiliary attachment for a tomography apparatus for conducting a tomogram-guided biopsy of a female breast, said attachment comprising:

first and second compression plates adapted for receiving a female breast therebetween;

means for moving said compression plates toward and away from each other for fixing a position of a breast therebetween;

each compression plate having a plurality of through-holes therein arranged to provide a plurality of substantially arbitrary access paths, each hole adapted to receive a biopsy needle therethrough for providing a guided access of said biopsy needle into a breast; between said compression plates; and each compression plate having a pressing surface and said through-holes in at least one of said compression plates being oriented obliquely, relative to a surface normal, toward a chest wall of a subject of said compressing surface and forming means for accessing a site in a breast adjacent a chest wall.

2. A stereotactic auxiliary attachment as claimed in claim 1 wherein said obliquely oriented through-holes are disposed at an angle of approximately 30° relative to said surface normal.

3. A stereotactic auxiliary attachment as claimed in claim 1 further comprising first and second frames for respectively removably receiving and holding said first and second compression plates.

4. A stereotactic auxiliary attachment as claimed in claim 1 further comprising marking means permanently allocated to at least one compression plate for generating a visible mark in a tomogram.

5. A stereotactic auxiliary attachment as claimed in claim 1 further comprising antenna means for obtaining nuclear magnetic resonance signals from said breast between said compression plates, said antenna means being oriented in a defined spatial relationship relative to said compression plates.

* * * * *